(12) United States Patent
Guillou et al.

(10) Patent No.: US 7,470,657 B2
(45) Date of Patent: Dec. 30, 2008

(54) CLEANSING COMPOSITION CONTAINING AN AMPHIPHILIC POLYMER

(75) Inventors: Veronique Guillou, Antony (FR); Isabelle Carton, Paris (FR)

(73) Assignee: L'Oreal, Clichy (FR)

( * ) Notice: Subject to any disclaimer, the term of this patent is extended or adjusted under 35 U.S.C. 154(b) by 1087 days.

(21) Appl. No.: 10/181,981

(22) PCT Filed: Jan. 8, 2002

(86) PCT No.: PCT/FR02/00048

§ 371 (c)(1), (2), (4) Date: Jul. 24, 2002

(87) PCT Pub. No.: WO02/055040

PCT Pub. Date: Jul. 18, 2002

(65) Prior Publication Data

US 2003/0050201 A1 Mar. 13, 2003

(30) Foreign Application Priority Data

Jan. 11, 2001 (FR) .................................. 01 00330

(51) Int. Cl.
- C11D 1/88 (2006.01)
- C11D 3/22 (2006.01)
- C11D 3/37 (2006.01)
- A61K 7/06 (2006.01)
- A61K 7/48 (2006.01)

(52) U.S. Cl. .................. 510/475; 510/127; 510/470; 510/535; 424/401; 424/70.1; 424/70.11; 424/70.21; 514/557; 514/562; 514/772

(58) Field of Classification Search ............ 510/127, 510/470, 475, 535; 424/401, 70.1, 70.11, 424/70.21; 514/557, 562, 772
See application file for complete search history.

(56) References Cited

U.S. PATENT DOCUMENTS

| 4,460,732 A | 7/1984 | Buscall et al. |
| 4,861,499 A | 8/1989 | Neff et al. |
| 5,089,578 A | 2/1992 | Valint et al. |
| 5,114,706 A | 5/1992 | Duvel |
| 5,464,452 A | 11/1995 | Johnson et al. |
| 6,123,960 A * | 9/2000 | Favre et al. ................. 424/450 |
| 6,645,476 B1 * | 11/2003 | Morschhauser et al. .... 424/70.1 |
| 2003/0036490 A1 * | 2/2003 | Lorant et al. ................. 510/130 |
| 2003/0050201 A1 * | 3/2003 | Guillou et al. ............... 510/130 |
| 2003/0108577 A1 * | 6/2003 | Lorant et al. ................. 424/401 |
| 2003/0157047 A1 * | 8/2003 | Lennon et al. ............ 424/70.11 |

FOREIGN PATENT DOCUMENTS

| EP | 0 406 042 | 1/1991 |
| EP | 0 750 899 | 1/1997 |
| EP | 0 815 843 | 1/1998 |
| EP | 1 055 406 | 11/2000 |
| JP | 08 252447 | 10/1996 |
| WO | 98 56333 | 12/1998 |
| WO | 00 31154 | 6/2000 |

OTHER PUBLICATIONS

U.S. Appl. No. 10/181,412, filed Jul. 23, 2002, Lorant, et al.
U.S. Appl. No. 10/181,983, filed Jul. 24, 2002, Lorant, et al.
U.S. Appl. No. 10/181,981, filed Jul. 24, 2002, Guillou, et al.
A. Kobayashi et al.: "Solubilization properties of N-substituted amphiphilic acrylamide copolymers" Journal of Applied Polymer Science., vol. 73, No. 12, pp. 2447-2453 Sep. 19, 1999.

* cited by examiner

Primary Examiner—Brian P Mruk
(74) Attorney, Agent, or Firm—Oblon, Spivak, McClelland, Maier & Neustadt, P.C.

(57) ABSTRACT

The present patent application relates to a cleansing composition comprising in an aqueous medium at least one surfactant selected from alkylpolyglycosides, maltose esters, glycerolated fatty alcohols, N-alkylglucamine derivatives, amido ether carboxylates, acetates, alaninates, aspartates, glycinates, citrates, galacturonates, fatty acid salts constituting soaps, phosphates, amphoteric and zwitterionic surfactants, and at least one amphiphilic polymer comprising at least one ethylenically unsaturated monomer containing a sulphonic group in free form or in partially or totally neutralized form and comprising at least one hydrophobic portion. The composition can especially constitute a foaming composition that has a good volume of foam by virtue of the presence of the amphiphilic polymer. The composition of the invention may especially be used in cosmetology or dermatology, as a cleansing product or make-up-removing product for the skin, the scalp and/or the hair.

45 Claims, No Drawings

CLEANSING COMPOSITION CONTAINING AN AMPHIPHILIC POLYMER

The invention relates to a foaming cleansing composition comprising a particular surfactant and an amphiphilic polymer comprising at least one ethylenically unsaturated monomer containing a sulphonic group in free form or in partially or totally neutralized form and comprising at least one hydrophobic portion. The invention also relates to the uses of the said composition in cosmetics or dermatology, especially as a cleansing product or a make-up-removing product for the skin, the scalp and/or the hair.

Cleansing the skin is very important for facial care. It must be as efficient as possible since greasy residues such as excess sebum, residues of cosmetic products used daily and make-up products, especially "waterproof" products, accumulate in the folds of the skin and can block the skin pores and lead to the appearance of spots.

It is known practice to use foaming detergent compositions to cleanse the skin. Their cleansing action is provided by the surfactants they contain, these surfactants placing the greasy residues and the pigments of the make-up products into suspension. These compositions are efficient and pleasant to use due to the fact that they foam, and the volume of foam is generally proportional to the surfactant concentration. However, the incorporation of an excessive amount of surfactants may be harmful to the satisfactory skin and eye tolerability of the compositions, especially for individuals with sensitive skin. Thus, in the field of foaming cleansing agents, it is sought to combine both foaming performance and tolerability.

Moreover, foaming compositions are generally quite fluid, which occasionally makes them difficult to handle, and it is difficult to thicken them while at the same time retaining good foaming properties, since the addition of thickeners to increase the viscosity generally has the consequence of reducing the volume of foam: it is usually said that the viscosity "kills" the foam.

There is thus still a need for a foaming composition that does not comprise an excessive amount of surfactant, and that has a good quality of foam and satisfactory viscosity, while at the same time having good eye and skin tolerability.

The Applicant has discovered, surprisingly, that it is possible to achieve the aim of the invention and to obtain a foaming composition that has both good cosmetic properties (foam qualities and satisfactory viscosity) and good tolerability properties by using a novel family of amphiphilic polymers and certain foaming surfactants.

Thus, one subject of the present patent application is a cleansing composition containing, in a physiologically acceptable aqueous medium, at least one surfactant chosen from alkylpolyglycosides, maltose esters, glycerolated fatty alcohols, N-alkylglucamine derivatives, amido ether carboxylates, acetates, alaninates, aspartates, glycinates, citrates, galacturonates, fatty acid salts constituting soaps, phosphates, amphoteric and zwitterionic surfactants, and at least one amphiphilic polymer comprising at least one ethylenically unsaturated monomer containing a sulphonic group in free form or in partially or totally neutralized form and comprising at least one hydrophobic part.

In the present patent application, the expression "physiologically acceptable medium" means a medium that is compatible with all keratin materials, such as the skin, including the scalp, the nails, mucous membranes, the eyes and the hair, or any other area of body skin. Moreover, it is an aqueous medium, that is to say a medium comprising an amount of water of at least 30% by weight relative to the total weight of the composition.

The viscosity of the compositions according to the invention may range, for example, from 0.001 to 100 poises (0.0001 to 10 Pa.s), preferably from 0.01 to 80 poises (0.001 to 8 Pa.s) and better still from 1 to 60 poises (0.1 to 6 Pa.s), measured at about 25° C. using a Rheomat RM180 viscometer from Rheometric Scientific, this machine being equipped with a different spindle depending on the viscosities, for example a spindle No. 2 for viscosity ranges of less than 7 poises, a spindle No. 3 for viscosity ranges from 2 to 40 poises and a spindle No. 4 for viscosity ranges from 20 poises to 80 poises.

The amphiphilic polymers used in the composition of the invention, especially those that are crosslinked, make it possible to obtain particularly satisfactory foam quality, without the addition of an excessive amount of foaming surfactant, whether this surfactant is nonionic, anionic, amphoteric or zwitterionic. These polymers especially make it possible to increase the volume of foam relative to the volume obtained with the surfactant without polymer or with a polymer other than the one used in accordance with the present patent application.

Thus, a subject of the present invention is also the use of an amphiphilic polymer comprising at least one ethylenically unsaturated monomer containing a sulphonic group in free form or in partially or totally neutralized form and comprising at least one hydrophobic portion, to increase the volume of foam of a composition containing at least one surfactant.

Other characteristics, aspects and advantages of the present invention will become apparent on reading the detailed description which follows.

Amphiphilic Polymers According to the Invention

The polymers in accordance with the invention are amphiphilic polymers comprising at least one ethylenically unsaturated monomer containing a sulphonic group in free form or partially or totally neutralized form and comprising at least one hydrophobic part.

The expression "amphiphilic polymer" means any polymer comprising both a hydrophilic part and a hydrophobic part and especially a fatty chain.

The hydrophobic part present in the polymers of the invention preferably contains from 6 to 50 carbon atoms, more preferably from 6 to 22 carbon atoms, even more preferably from 6 to 18 carbon atoms and more particularly from 12 to 18 carbon atoms.

Preferably, the polymers in accordance with the invention are partially or totally neutralized with a mineral base (sodium hydroxide, potassium hydroxide or aqueous ammonia) or an organic base such as mono-, di- or triethanolamine, an aminomethylpropanediol, N-methylglucamine, basic amino acids, for instance arginine and lysine, and mixtures of these compounds.

The amphiphilic polymers in accordance with the invention generally have a number-average molecular weight ranging from 1000 to 20 000 000 g/mol, preferably ranging from 20 000 to 5 000 000 and even more preferably from 100 000 to 1 500 000 g/mol.

The amphiphilic polymers according to the invention may or may not be crosslinked. Crosslinked amphiphilic polymers are preferably chosen.

When they are crosslinked, the crosslinking agents may be chosen from compounds containing olefinic polyunsaturation commonly used for the crosslinking of polymers obtained by free-radical polymerization.

Mention may be made, for example, of divinylbenzene, diallyl ether, dipropylene glycol diallyl ether, polyglycol diallyl ethers, triethylene glycol divinyl ether, hydroquinone diallyl ether, ethylene glycol di(meth)acrylate or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allyl or vinyl ethers of polyfunctional alcohols, and also allylic esters of phosphoric and/or vinylphosphonic acid derivatives, or mixtures of these compounds.

Methylenebisacrylamide, allyl methacrylate or trimethylolpropane triacrylate (TMPTA) will be used more particularly. The degree of crosslinking will generally range from 0.01 mol % to 10 mol % and more particularly from 0.2 mol % to 2 mol % relative to the polymer.

The ethylenically unsaturated monomers containing a sulphonic group are chosen especially from vinylsulphonic acid, styrenesulphonic acid, (meth)acrylamido($C_1$-$C_{22}$)alkylsulphonic acids, N—($C_1$-$C_{22}$) alkyl (meth)acrylamido ($C_1$-$C_{22}$) alkylsulphonic acids, for instance undecylacrylamidomethanesulphonic acid, and also partially or totally neutralized forms thereof.

(Meth)acrylamide($C_1$-$C_{22}$)alkylsulphonic acids such as, for example, acrylamidomethanesulphonic acid, acrylamidoethanesulphonic acid, acrylamidopropane-sulphonic acid, 2-acrylamido-2-methylpropanesulphonic acid, methacrylamido-2-methylpropanesulphonic acid, 2-acrylamido-n-butanesulphonic acid, 2-acrylamido-2,4,4-trimethylpentanesulphonic acid, 2-methacrylamidododecylsulphonic acid or 2-acrylamido-2,6-dimethyl-3-heptanesulphonic acid, and also partially or totally neutralized forms thereof, will more preferably be used.

2-Acrylamido-2-methylpropanesulphonic acid (AMPS), and also its partially or totally neutralized forms, will more particularly be used.

The amphiphilic polymers in accordance with the invention may be chosen especially from random amphiphilic polymers of AMPS modified by reaction with a $C_6$-$C_{22}$ n-monoalkylamine or di-n-alkylamine, such as those described in patent application WO-00/31154 (forming an integral part of the content of the description). These polymers may also contain other ethylenically unsaturated hydrophilic monomers chosen, for example, from (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

The preferred polymers of the invention are chosen from amphiphilic copolymers of AMPS and of at least one ethylenically unsaturated hydrophobic monomer comprising at least one hydrophobic portion containing from 6 to 50 carbon atoms, more preferably from 6 to 22 carbon atoms, even more preferably from 6 to 18 carbon atoms and more particularly 12 to 18 carbon atoms.

These same copolymers may also contain one or more ethylenically unsaturated monomers not comprising a fatty chain, such as (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

These copolymers are described especially in patent application EP-A-750 899, patent U.S. Pat. No. 5 089 578 and in the following publications from Yotaro Morishima:

"Self-assembling amphiphilic polyelectrolytes and their nanostructures—Chinese Journal of Polymer Science Vol. 18, No. 40, (2000), 323-336";

"Micelle formation of random copolymers of sodium 2-(acrylamido)-2-methylpropanesulfonate and a nonionic surfactant macromonomer in water as studied by fluorescence and dynamic light scattering—Macromolecules 2000, Vol. 33, No. 10-3694-3704";

"Solution properties of micelle networks formed by nonionic moieties covalently bound to a polyelectrolyte: salt effects on Theological behavior—Langmuir, 2000, Vol. 16, No. 12, 5324-5332";

"Stimuli responsive amphiphilic copolymers of sodium 2-(acrylamido)-2-methylpropanesulfonate and associative macromonomers—Polym. Preprint, Div. Polym. Chem. 1999, 40(2), 220-221".

The ethylenically unsaturated hydrophobic monomers of these particular copolymers are preferably chosen from the acrylates or acrylamides of formula (I) below:

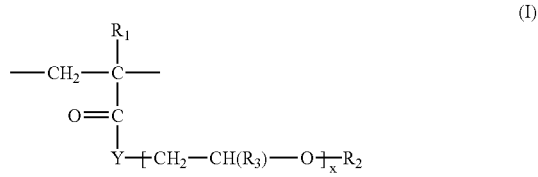

in which $R_1$ and $R_3$, which may be identical or different, denote a hydrogen atom or a linear or branched $C_1$-$C_6$ alkyl radical (preferably methyl); Y denotes O or $NR_1$, $R_1$ having the meaning given above; $R_2$ denotes a hydrophobic hydrocarbon-based radical containing at least from 6 to 50 carbon atoms, more preferably from 6 to 22 carbon atoms, even more preferably from 6 to 18 carbon atoms and more particularly from 12 to 18 carbon atoms; x denotes a number of moles of alkylene oxide and ranges from 0 to 100.

The radical $R_2$ is preferably chosen from linear $C_6$-$C_{18}$ alkyl radicals (for example n-hexyl, n-octyl, n-decyl, n-hexadecyl and n-dodecyl) and branched or cyclic $C_6$-$C_{18}$ alkyl radicals (for example cyclododecane ($C_{12}$) or adamantane ($C_{10}$)); $C_6$-$C_{18}$ alkylperfluoro radicals (for example the group of formula —($CH_2$)$_2$—($CF_2$)$_9$—$CF_3$); the cholesteryl radical ($C_{27}$) or a cholesterol ester residue, for instance the cholesteryl oxyhexanoate group; aromatic polycyclic groups, for instance naphthalene or pyrene. Among these radicals, the ones that are more particularly preferred are linear alkyl radicals and more particularly the n-dodecyl or n-hexadecyl radical.

According to one particularly preferred form of the invention, the monomer of formula (I) comprises at least one alkylene oxide unit ($x \geqq 1$) and preferably a polyoxyalkylenated chain. The polyoxyalkylenated chain preferably consists of ethylene oxide units and/or propylene oxide units and even more particularly consists of ethylene oxide units. The number of oxyalkylenated units (or moles of alkylene oxide) generally ranges from 3 to 100, more preferably from 3 to 50 and even more preferably from 7 to 25.

Among these polymers, mention may be made of:
crosslinked or non-crosslinked, neutralized or non-neutralized copolymers comprising from 15% to 60% by weight of AMPS units and from 40% to 85% by weight of ($C_8$-$C_{16}$) alkyl (meth) acrylamide units or of ($C_8$-$C_{16}$) alkyl (meth)acrylate units relative to the polymer, such as those described in patent application EP-A-750 899;

terpolymers comprising from 10 mol % to 90 mol % of acrylamide units, from 0.1 mol % to 10 mol % of AMPS units and from 5 mol % to 80 mol % of n-($C_6$-$C_{18}$) alkylacrylamide units, such as those described in U.S. Pat. No. 5,089,578.

Mention may also be made of copolymers of totally neutralized AMPS and of dodecyl or n-hexadecyl methacrylate, and also crosslinked and non-crosslinked copolymers of AMPS and of n-dodecylmethacrylamide, such as those described in the Morishima articles mentioned above.

Mention will be made more particularly of the copolymers consisting of 2-acrylamido-2-methylpropanesulphonic acid (AMPS) units of formula (II) below:

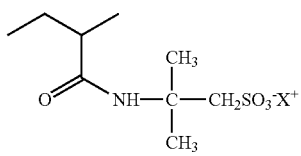

(II)

in which $X^+$ is a proton, an alkali metal cation, an alkaline-earth metal cation or the ammonium ion, and of units of formula (III) below:

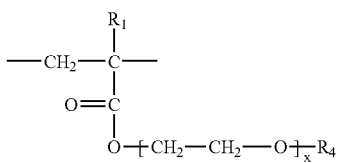

(III)

in which x denotes an integer ranging from 3 to 100, preferably from 5 to 80 and more preferably from 7 to 25; $R_1$ has the same meaning as that given above in formula (I) and $R_4$ denotes a linear or branched $C_6$-$C_{22}$ and more preferably $C_{10}$-$C_{22}$ alkyl.

The polymers that are particularly preferred are those for which, in formula (III), x=25, $R_1$ denotes methyl and $R_4$ represents n-dodecyl; they are described in the Morishima articles mentioned above. Other preferred polymers are those for which x=25, $R_1$ denotes methyl and $R_4$ represents n-hexadecyl or n-octadecyl.

The polymers for which $X^+$ denotes sodium or ammonium are more particularly preferred.

The preferred amphiphilic polymers in accordance with the invention may be obtained according to the standard free-radical polymerization processes in the presence of one or more initiators such as, for example, azobisisobutyronitrile (AIBN), azobisdimethylvaleronitrile, 2,2-azobis[2-amidinopropane]hydrochloride (ABAH=2,2-AzoBis[2-Amidino-propane]Hydrochloride), organic peroxides such as dilauryl peroxide, benzoyl peroxide, tert-butyl hydroperoxide, etc., mineral peroxide compounds such as potassium persulphate or ammonium persulphate, or $H_2O_2$ optionally in the presence of reducing agents.

The amphiphilic polymers in accordance with the invention are obtained especially by free-radical polymerization in tert-butanol medium in which they precipitate. Using precipitation polymerization in tert-butanol, it is possible to obtain a particle size distribution of the polymer that is particularly favourable for its uses.

The size distribution of the polymer particles may be determined, for example, by laser diffraction or image analysis. An advantageous distribution for this type of polymer, determined by image analysis, is as follows: 60.2% less than 423 microns, 52.0% less than 212 microns, 26.6% less than 106 microns, 2.6% less than 45 microns and 26.6% greater than 850 microns.

The reaction may be performed at a temperature of between 0 and 150° C., preferably between 10 and 100° C., either at atmospheric pressure or under reduced pressure. It may also be performed under inert atmosphere, and preferably under nitrogen.

According to this process 2-acrylamido-2-methylpropanesulphonic acid (AMPS) or a sodium or ammonium salt thereof was especially polymerized with a (meth)acrylic acid ester and a $C_{10}$-$C_{18}$ alcohol oxyethylenated with 8 mol of ethylene oxide (Genapol® C-080 from the company Hoechst/Clariant), a $C_{11}$ oxo alcohol oxyethylenated with 8 mol of ethylene oxide (Genapol® UD-080 from the company Hoechst/Clariant), a $C_{12}$-$C_{14}$ alcohol oxyethylenated with 3 mol of ethylene oxide (Genapol® LA-030 from the company Hoechst/Clariant), a $C_{11}$ oxo alcohol oxyethylenated with 7 mol of ethylene oxide (Genapol® UD-070 from the company Hoechst/Clariant), a $C_{12}$-$C_{14}$ alcohol oxyethylenated with 7 mol of ethylene oxide (Genapol® LA-070 from the company Hoechst/Clariant), a $C_{12}$-$C_{14}$ alcohol oxyethylenated with 9 mol of ethylene oxide (Genapol® LA-090 from the company Hoechst/Clariant), a $C_{12}$-$C_{14}$ alcohol oxyethylenated with 11 mol of ethylene oxide (Genapol® LA-110 from the company Hoechst/Clariant), a $C_{16}$-$C_{18}$ alcohol oxyethylenated with 8 mol of ethylene oxide (Genapol® T-080 from the company Hoechst/Clariant), a $C_{16}$-$C_{18}$ alcohol oxyethylenated with 15 mol of ethylene oxide (Genapol® T-150 from the company Hoechst/Clariant), a $C_{16}$-$C_{18}$ alcohol oxyethylenated with 11 mol of ethylene oxide (Genapol® T-110 from the company Hoechst/Clariant), a $C_{16}$-$C_{18}$ alcohol oxyethylenated with 20 mol of ethylene oxide (Genapol® T-200 from the company Hoechst/Clariant), a $C_{16}$-$C_{18}$ alcohol oxyethylenated with 25 mol of ethylene oxide (Genapol® T-250 from the company Hoechst/Clariant), a $C_{18}$-$C_{22}$ alcohol oxyethylenated with 25 mol of ethylene oxide and/or a $C_{16}$-$C_{18}$ iso alcohol oxyethylenated with 25 mol of ethylene oxide.

The molar % concentration of the units of formula (II) and of the units of formula (III) in the polymers according to the invention will vary as a function of the desired cosmetic use and of the desired Theological properties of the formulation. It may range between 0.1 mol % and 99.9 mol %.

Preferably, for the most hydrophobic polymers, the molar proportion of units of formula (I) or (III) ranges from 50.1% to 99.9%, more particularly from 70% to 95% and even more particularly from 80% to 90%.

Preferably, for the sparingly hydrophobic polymers, the molar proportion of units of formula (I) or (III) ranges from 0.1% to 50%, more particularly from 1% to 25% and even more particularly from 3% to 20%.

The monomer distribution in the polymers of the invention may be, for example, alternating, block (including multiblock) or random.

According to the invention, it is preferable for the polymers to contain heat-sensitive pendant chains and for the aqueous solution thereof to have a viscosity that, beyond a certain threshold temperature, increases or remains virtually constant as the temperature increases.

Even more particularly, the preferred polymers are those whose aqueous solution has a viscosity that is low below a first threshold temperature and that, above this first threshold temperature, increases to a maximum as the temperature increases, and that, above a second threshold temperature, decreases again as the temperature increases. In this perspective, it is preferable for the viscosity of the polymer solutions below the first threshold temperature to be from 5% to 50%, in particular from 10% to 30% of the maximum viscosity at the second threshold temperature.

These polymers preferably lead in water to a phenomenon of demixing by heating, reflected by curves showing, as a function of the temperature and the concentration, a minimum known as the LCST (Lower Critical Solution Temperature).

The viscosities (measured at 25° C. using a Brookfield viscometer, needle No. 7) of the aqueous 1% solutions preferably range from 20 000 mPa.s to 100 000 mpa.s and more particularly from 60 000 mPa.s to 70 000 mPa.s.

According to one preferred embodiment of the invention, the amphiphilic polymers used in the cleansing composition are crosslinked.

The amphiphilic polymers in accordance with the invention are present in the compositions in concentrations ranging from 0.01% to 50% by weight of active material, more preferably from 0.1% to 20%, even more preferably from 0.2% to 10% by weight and even more particularly from 0.25% to 5% by weight of active material relative to the total weight of the composition.

Surfactants

The surfactants used in the composition are generally foaming surfactants chosen from alkylpolyglycosides (abbreviated as APG), maltose esters, glycerolated fatty alcohols, N-alkylglucamine derivatives, amido ether carboxylates, acetates, alaninates, aspartates, glycinates, citrates, galacturonates, fatty acid esters constituting soaps, phosphates, amphoteric and zwitterionic surfactants, and mixtures thereof. One or more other optional additional surfactants chosen from nonionic and anionic surfactants, and mixtures thereof, may optionally be added to these surfactants.

I. The foaming surfactant(s) that may be used as surfactants in the composition of the invention may be chosen from the following surfactants:

1) Alkylpolyglycosides which may be represented more particularly by the general formula (IV) below

R—O—(G)$_x$ (IV)

in which R represents a linear or branched, saturated or unsaturated alkyl radical containing from 6 to 30 carbon atoms, G represents a reduced sugar containing from 5 to 6 carbon atoms, and x denotes a value ranging from 1 to 15.

Alkylpolyglycosides that are preferred according to the present invention are compounds of formula (IV) in which R more particularly denotes an alkyl radical containing from 8 to 16 carbon atoms, G denotes glucose, fructose or galactose, x is a value ranging from 1 to 4 and more particularly from 1 to 3. According to one preferred embodiment of the invention, alkylpolyglucosides are used, that is to say compounds of formula (IV) in which G denotes glucose, with x preferably having a value ranging from 1.2 to 3.

Examples of alkylpolyglucosides that may be mentioned include decylglucoside (alkyl-C9/C11-polyglucoside (1.4)), for instance the product sold under the name Mydol 10 by the company Kao Chemicals, the product sold under the name Plantaren 2000 UP and Plantacare 2000 UP by the company Henkel, and the product sold under the name Oramix NS10 by the company SEPPIC; caprylyl/capryl glucoside, for instance the product sold under the name Oramix CG110 by the company SEPPIC or under the name Lutensol GD70 by the company BASF; laurylglucoside, for instance the products sold under the names Plantaren 1200 N and Plantacare 1200 by the company Henkel; and coco-glucoside, for instance the product sold under the name Plantacare 818/UP by the company Henkel, and mixtures thereof.

2) Maltose derivatives, which are, for example, those described in document EP-A-566 438, such as O-octanoyl-6'-D-maltose, or Q-dodecanoyl-6'-D-maltose described in document FR-A-2 739 556.

3) Polyglycerolated fatty alcohols, which are polyglyceryl alkyl ethers, with an alkyl group containing from 8 to 30 carbon atoms and preferably from 10 to 22 carbon atoms. Examples of polyglycerolated fatty alcohols that may be mentioned include polyglycerolated dodecanediol (3.5 mol of glycerol) or Polyglyceryl-3 hydroxylauryl Ether (CTFA name) sold under the name Chimexane NF by the company Chimex.

4) N-Alkylglucamine derivatives such as, in particular, N-methyl-2-ethylhexyloxycarbonylglucamine.

5) Amido ether carboxylates (AEC), such as oxyethylenated sodium laurylamido ether carboxylate (3 EO) sold under the name Akypo Foam 30® by the company Kao Chemicals.

6) Acetates, such as sodium 2-(2-hydroxyalkyloxy)acetate sold under the name Beaulight Shaa by the company Sanyo.

7) Alaninates, for instance sodium N-lauroyl-N-methylamidopropionate sold under the name Sodium Nikkol Alaninate LN 30® by the company Nikkol or sold under the name Alanone Ale® by the company Kawaken, and N-lauroyl-N-methylalanine triethanolamine sold under the name Alanone Alta® by the company Kawaken.

8) Aspartates, for instance the mixture of triethanolamine N-lauroylaspartate/triethanolamine N-myristoylaspartate, sold under the name Asparack® by the company Mitsubishi.

9) Glycinates, for instance potassium N-cocoylglycinate or sodium N-cocoylglycinate sold under the names Amilite GCS-12® and Amilite GCK-12® by the company Ajinomoto.

10) Citrates, such as the citric monoester of oxyethylenated coco alcohols (9 EO), sold under the name Witconol EC 1129 by the company Goldschmidt.

11) Galacturonates, such as sodium dodecyl d-galactoside uronate sold by the company Soliance.

12) Fatty acid salts constituting soaps, and, for example, those with a fatty chain containing from 6 to 22 carbon atoms, neutralized with an organic or mineral base such as potassium hydroxide or sodium hydroxide, and organic bases, for instance triethanolamine, N-methylglucamine, lysine or arginine. Mention may especially be made of the potassium and sodium salts of C10 to C22 fatty acids and especially the potassium salts of lauric acid, of palmitic acid and of stearic acid.

13) Phosphates, and especially monoalkyl phosphates and dialkyl phosphates such as, for example, lauryl monophosphate sold under the name Map 20® by the company Kao Chemicals, the potassium salt of dodecylphosphoric acid, mono/diester (predominant) mixture sold under the name Crafol AP-31® by the company Pulcra, and octylphosphoric acid, mono/diester mixture sold under the name Crafol AP-20® by the company Pulcra.

14) Amphoteric and zwitterionic surfactants, which may be chosen, for example, from betaines, N-alkylamidobetaines and derivatives, sultaines and alkyl polyaminocarboxylates; and mixtures thereof.

Examples of betaines that may be mentioned include lauryl betaine sold under the name Genagen KB® by the company Clariant, oxyethylenated lauryl betaine (10 EO) sold under the name Lauryl Ether(10 OE) Betaine® by the company Shin Nihon Rica, oxyethylenated stearyl betaine (10 EO) sold under the name Stearyl Ether(10 OE) Betaine® by the company Shin Nihon Rica, cocobetaine sold under the name Empigen BB/FL by the company Albright & Wilson or Dehyton AB30 by the company Cognis.

Examples of N-alkylamido betaines and derivatives that may be mentioned include cocamidopropyl betaine sold under the name Lebon 2000 HG® by the company Sanyo, or sold under the name Empigen BB® by the company Albright & Wilson, lauramidopropyl betaine sold under the name Rewoteric AMB12P® by the company Witco, and N-disodium N-carboxyethoxyethyl N-cocoylamidoethyl aminoacetate, sold under the name Miranol C2M Concentre NP® by the company Rhodia Chimie.

Examples of sultaines that may be mentioned include cocoyl amidopropyl hydroxysulphobetaine sold under the name Crosultaine C-50® by the company Croda.

Examples of alkyl polyaminocarboxylates (APAC) that may be mentioned include sodium cocoyl polyaminocarboxylate, sold under the name Ampholak 7 CX/C®, Ampholak 7 CX® by the company Akzo Nobel, sodium stearyl polyamidocarboxylate, sold under the name Ampholak 7 TX/C® by the company Akzo Nobel, and sodium carboxymethyloleyl polypropylamine, sold under the name Ampholak XO7/C® by the company Akzo Nobel.

II. The optional additional surfactants that may be added to the composition of the invention may be chosen, for example, from polycondensates of ethylene oxide and of propylene oxide on an alkyl chain; fatty acid esters of polyols; alkoxylated alkamides; poiyoxyethylenated carboxylic acid salts; sarcosinates; glutamates; alkyl sulphates; alkyl ether sulphates; sulphonates; isethionates; taurates; sulphosuccinates; alkylsulphoacetates; polypeptides; anionic derivatives of alkyl polyglucoside; and mixtures thereof.

Fatty acid esters of polyols that may be mentioned include those with a fatty chain containing from 8 to 30 carbon atoms and preferably from 10 to 22 carbon atoms. The polyol may especially be glycerol or glycerol polymers (polyglycerol) containing several glycerol units. Examples of fatty acid esters of polyols that may be mentioned include polyglyceryl monolaurate, such as the product sold under the name Sunsoft M-12J by the company Taiyo Kagaku.

Alkoxylated alkamides that may especially be mentioned include ethoxylated alkamides, for instance PEG-5 Cocamide (CTFA name) and in particular the product sold under the name Genagen CA-050 by the company Clariant.

Polyoxyethylenated carboxylic acid salts that may especially be mentioned include oxyethylenated (6 EO) sodium lauryl ether carboxylate (65/25/10 C12-14-16) sold under the name Akypo Soft 45 NV® by the company Kao Chemicals, polyoxyethylenated and carboxymethylated fatty acids derived from olive oil, for instance the product sold under the name Olivem 400® by the company Biologia E Tecnologia, and oxyethylenated (6 EO) sodium tridecyl ether carboxylate sold under the name Nikkol ECTD-6NEX® by the company Nikkol.

Examples of sarcosinates that may be mentioned include sodium lauroyl sarcosinate sold under the name Sarkosyl NL 97® by the company CIBA or sold under the name Oramix L 30® by the company SEPPIC, sodium myristoyl sarcosinate sold under the name Nikkol Sarcosinate MN® by the company Nikkol, and sodium palmitoyl sarcosinate sold under the name Nikkol Sarcosinate PN® by the company Nikkol.

Examples of glutamates that may be mentioned include triethanolamine monococoyl glutamate sold under the name Acylglutamate CT-12® by the company Ajinomoto, and triethanolamine lauroyl glutamate sold under the name Acylglutamate LT-12® by the company Ajinomoto.

Examples of alkyl sulphates and alkyl ether sulphates that may be mentioned include oxyethylenated or non-oxyethylenated alkyl sulphates, for instance sodium lauryl ether sulphate (mixture of C12-14 in a 70/30 weight ratio) (2.2 EO), sold under the name Sipon AOS 225® by the company Henkel, ammonium lauryl ether sulphate (mixture of C12-14 in a 70/30 weight ratio) (3 EO) sold under the name Sipon LEA 370® by the company Henkel, ammonium alkyl (C12-14) ether (9 EO) sulphate sold under the name Rhodapex AB/20® by the company Rhodia Chimie, and the mixture of sodium and magnesium lauryl and oleyl ether sulphate, sold under the name Empicol BSD 52 by the company Albright & Wilson.

Examples of sulphonates that may be mentioned include α-olefin sulphonates, for instance sodium α-olefin sulphonate (C14-16) sold under the name Bio-Terge AS-40® by the company Stepan, or sold under the name Witconate AOS Protege® or Sulframine AOS PH 12® by the company Witco, or sold under the name Bio-Terge AS-40 CG® by the company Stepan, and secondary sodium olefin sulphonate sold under the name Hostapur SAS 30® by the company Clariant.

An example of isethionates that may be mentioned is sodium cocoyl isethionate sold under the name Jordapon CI P® by the company Jordan.

Examples of taurates that may be mentioned include the sodium salt of palm kernel oil methyltaurate, sold under the name Hostapon CT Pate® by the company Clariant, sodium N-cocoyl N-methyltaurate sold under the name Hostapon LT-SF® by the company Clariant or sold under the name Nikkol CMT-30-T® by the company Nikkol, and sodium palmitoyl methyltaurate sold under the name Nikkol PMT® by the company Nikkol.

Examples of sulphosuccinates that may be mentioned include oxyethylenated (3 EO) lauryl alcohol monosulphosuccinate (70/30 C12-14) sold under the name Setacin 103 Special® by the company Zschimmer Schwarz, or Rewopol SB-FA 30 K 4® by the company Witco, the disodium salt of a hemi-sulphosuccinate of C12-C14 alcohols, sold under the name Setacin F Special Paste® by the company Zschimmer Schwarz, oxyethylenated (2 EO) disodium oleamido sulphosuccinate sold under the name Standapol SH 135® by the company Henkel, and oxyethylenated (5 EO) lauramide monosulphosuccinate sold under the name Lebon A-5000® by the company Sanyo.

Examples of alkyl sulphoacetates that may be mentioned include the mixture of sodium lauryl sulphoacetate and disodium lauryl ether sulphosuccinate, sold under the name Stepan-Mild LSB by the company Stepan.

Polypeptides that may be used include those obtained by condensation of a fatty chain onto the amino acids of wheat and oats, such as, for example, potassium-lauroyl hydrolyzed wheat protein, this product being sold under the name Aminofoam W OR® by the company Croda, the triethanolamine salt of cocoyl hydrolyzed soybean protein, sold under the name May-Tein SY® by the company Maybrook, the sodium salt of lauroyl amino acids of oats, sold under the name Proteol Oat® by the company SEPPIC, collagen hydrolysate grafted onto coconut fatty acid, sold under the name Geliderm 3000® by the company Deutsche Gelatine, and soybean proteins acylated with hydrogenated coconut acids, this product being sold under the name Proteol VS 22® by the company SEPPIC.

Anionic derivatives of alkyl polyglucoside that may be mentioned include the citrates, tartrates, sulphosuccinates, carbonates and glycerol ethers, obtained from alkyl polyglucosides, such as, for example, the sodium salt of cocoyl polyglucoside (1.4) tartaric ester, sold under the name Eucarol AGE-ET® by the company Cesalpinia, the disodium salt of cocoyl polyglucoside (1.4) sulphosuccinic ester, sold under the name Essai 512 MP® by the company SEPPIC, and the sodium salt of cocoyl polyglucoside (1.4) (1.4) citric ester, sold under the name Eucarol AGE-EC® by the company Cesalpinia.

The composition may contain a total amount of surfactants (including the additional surfactants) ranging from 0.1% to 50% by weight of active material, preferably from 0.2% to 35% and better still from 0.5% to 20% by weight of active material relative to the total weight of the composition.

According to one particular embodiment of the invention, the composition contains at least, as surfactant, an alkylpolyglycoside, and the amount of alkylpolyglycoside(s) preferably represents from 0.1% to 100% and better still from 10% to 100% by weight relative to the total weight of surfactants.

The physiologically acceptable medium for the composition of the invention comprises water. The amount of water may range from 30% to 99.85% by weight and preferably from 30% to 95% by weight relative to the total weight of the composition. This medium may contain, besides water, one or more solvents chosen from lower alcohols containing from 1 to 8 carbon atoms, such as ethanol; polyols such as glycerol; glycols, for instance butylene glycol, isoprene glycol, propylene glycol, or polyethylene glycols such as PEG-8; sorbitol; sugars such as glucose, fructose, maltose, lactose or sucrose; and mixtures thereof. The amount of solvent(s) in the composition of the invention may range from 0.5% to 30% by weight and preferably from 1% to 20% by weight relative to the total weight of the composition.

The composition of the invention preferably has a pH that is compatible with the skin, that is to say preferably ranging from 3 to 9 and better still from 4 to 8.

The compositions of the invention may contain adjuvants commonly used in cosmetics, chosen from fragrances, preserving agents, sequestering agents (EDTA), pigments, nacres, mineral or organic fillers, pH regulators, soluble colorants, sunscreens, active agents, cationic, anionic or amphoteric polymers other than the polymer forming the subject of the invention, and fatty substances (oils, fatty alcohols, fatty acids or waxes). The amounts of these various adjuvants are those conventionally used in the field under consideration, for example from 0.01% to 20% of the total weight of the composition. These adjuvants and the concentrations thereof should be such that they do not modify the property desired for the composition of the invention.

The composition according to the invention may be in any presentation form that is suitable for topical use, and especially in the form of fluids, gels and O/W emulsions (oily phase dispersed in an aqueous phase) or W/O emulsions (aqueous phase dispersed in an oily phase) or multiple emulsions. They are preferably in gel form.

The composition of the invention may also optionally contain at least one oily phase comprising one or more emollient and/or make-up-removing oils.

As oils which can be used in the composition of the invention, mention may be made for example of:
hydrocarbon-based oils of animal origin, such as perhydrosqualene;
hydrocarbon-based plant-origin oils, such as liquid triglycerides of fatty acids of 4 to 10 carbon atoms, such as heptanoic or octanoic acid triglycerides or alternatively, for example, sunflower oil, corn oil, soybean oil, marrow oil, grapeseed oil, sesame oil, hazelnut oil, apricot oil, macadamia oil, arara oil, castor oil, avocado oil, caprylic/capric acid triglycerides such as those sold by the company Stearineries Dubois or those sold under the names Miglyol 810, 812 and 818 by the company Dynamit Nobel, jojoba oil or karite butter;
synthetic esters and ethers in particular of fatty acids, such as the oils of formulae $R^1COOR^2$ and $R^1OR^2$ in which $R^1$ represents a fatty acid residue containing from 8 to 29 carbon atoms and $R^2$ represents a branched or unbranched hydrocarbon-based chain containing from 3 to 30 carbon atoms, such as, for example, purcellin oil, isononyl isononanoate, isopropyl myristate, 2-ethylhexyl palmitate, 2-octyldodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate, and fatty alcohol heptanoates, octanoates and decanoates; polyol esters such as propylene glycol dioctanoate, neopentyl glycol diheptanoate and diethylene glycol diisononanoate; and pentaerythritol esters such as pentaerythrityl tetraisostearate;
linear or branched hydrocarbons of mineral or synthetic origin, such as volatile or non-volatile liquid paraffins and derivatives thereof, petroleum jelly, polydecenes or hydrogenated polyisobutene such as parleam;
natural or synthetic essential oils such as, for example, eucalyptus oil, hybrid lavender oil, lavender oil, vetiver oil, Litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil;
fatty alcohols containing from 8 to 26 carbon atoms, such as cetyl alcohol, stearyl alcohol, and the mixture thereof (cetylstearyl alcohol), octyldodecanol, 2-butyloctanol, 2-hexyldecanol, 2-undecylpentadecanol, oleyl alcohol or linoleyl alcohol;
partially hydrocarbon-based and/or silicone-based fluoro oils such as those described in document JP-A-2-295 912;
silicone oils such as volatile or non-volatile polydimethylsiloxanes (PDMSs) containing a linear or cyclic silicone chain, which are liquid or pasty at room temperature, in particular cyclopolydimethylsiloxanes (cyclomethicones) such as cyclohexasiloxane; polydimethylsiloxanes comprising alkyl, alkoxy or phenyl groups, pendant or at the end of a silicone chain, these groups containing from 2 to 24 carbon atoms; phenylsilicones such as phenyl trimethicones, phenyl dimethicones, phenyltrimethyl-siloxydiphenylsiloxanes, diphenyl dimethicones, diphenylmethyldiphenyltrisiloxanes, 2-phenylethyl trimethyisiloxysilicates and polymethylphenylsiloxanes;

mixtures thereof.

The term "hydrocarbon-based oil" in the list of abovementioned oils embraces any oil comprising predominantly carbon and hydrogen atoms, and optionally ester, ether, fluoro, carboxylic acid and/or alcohol groups.

Among the oils indicated above, the make-up-removing oils are more particularly fatty acid esters containing at least 12 carbon atoms. These esters are preferably obtained from a straight-chain or branched-chain alcohol containing from 1 to 17 carbon atoms and from a straight-chain or branched-chain fatty acid containing at least 12 carbon atoms and preferably from 14 to 22 carbon atoms. They are preferably mono- or diesters. Examples of make-up-removing oils that may be mentioned include 2-ethylhexyl palmitate (or octyl palmitate), 2-ethylhexyl myristate (or octyl myristate), isopropyl palmitate, isopropyl myristate, diisopropyl adipate, dioctyl adipate, 2-ethylhexyl hexanoate, ethyl laurate, methyl myristate, octyldodecyl octanoate, isodecyl neopentanoate, ethyl myristate, myristyl propionate, 2-ethylhexyl 2-ethylhexanoate, 2-ethylhexyl octanoate, 2-ethylhexyl caprate/caprylate, methyl palmitate, butyl myristate, isobutyl myristate, ethyl palmitate, isohexyl laurate, hexyl laurate and isopropyl isostearate, and mixtures thereof.

The other fatty substances which may be present in the oily phase are, for example, fatty acids containing from 8 to 30 carbon atoms, for instance stearic acid, lauric acid, palmitic acid and oleic acid; waxes, for example lanolin, beeswax, carnauba wax, candelilla wax, paraffin wax, lignite wax or microcrystalline waxes, ceresine or ozokerite, synthetic waxes, for instance polyethylene waxes and Fischer-Tropsch waxes; gums such as silicone gums (dimethiconol); silicone resins such as trifluoromethyl-C1-4-alkyldimethicone and trifluoropropyldimethicone; and silicone elastomers, for instance the products sold under the names "KSG" by the company Shin-Etsu, under the names "Trefil", "BY29" or "EPSX" by the company Dow Corning or under the names "Gransil" by the company Grant Industries.

These fatty substances may be chosen in a varied manner by a person skilled in the art in order to prepare a composition having the desired properties, for example consistency or texture properties.

When it is present, the amount of oily phase may range, for example, from 0.01% to 50% by weight and preferably from 0.1% to 30% by weight relative to the total weight of the composition.

To obtain more or less fluid compositions, it is possible to incorporate into the compositions of the invention, besides the polymer described above, one or more thickeners, especially polymers, in concentrations ranging, for example, from 0.05% to 10% by weight of active material, preferably from 0.2% to 5% by weight and better still from 0.2% to 2% by weight relative to the total weight of the composition.

Examples of thickeners that may be mentioned include mineral salts such as sodium chloride; oxyethylenated molecules and especially ethoxylated alkyl or acyl derivatives of polyols which may be, in particular, oxyethylenated derivatives of fatty acid esters or of fatty alcohol ethers and of a polyol such as glycerol, sorbitol, glucose or pentaerythritol. Examples of compounds of this type that may be mentioned include oxyethylenated (200 EO) glyceryl stearate, such as the product sold under the name Simulsol 220 TM® by the company SEPPIC, oxyethylenated (150 EO) pentaerythrityl tetrastearate, such as the product sold under the name Crothix® by the company Croda, oxyethylenated (120 EO) methylglucose dioleate, such as the product sold under the name Glucamate DOE-120 Vegetal® by the company Amerchol, or oxyethylenated (160 EO) sorbitan triisostearate, such as the product sold under the name Rheodol TW IS399C by the company Kao Chemicals.

The compositions according to the invention generally have the appearance of a gel or a cream, which may be transparent. In addition, these compositions are stable and rinse off very well (very good rinsability). They may especially constitute a foaming composition, having a good volume of foam by virtue of the presence of the amphiphilic polymer. These compositions may be used in particular in cosmetics or dermatology, and they may constitute, for example, a cleansing product and/or a make-up-removing product for the skin, the scalp and/or the hair, a shampoo for the hair, a scrubbing product and/or an exfoliant product for the skin.

Another subject of the invention consists of the cosmetic use of the composition as defined above as a cleansing product and/or a make-up-removing product for the skin, the scalp and/or the hair, and/or as a shampoo and/or as a scrubbing product and/or an exfoliant product for the skin.

As a cleansing product and/or a make-up-removing product for the skin, the compositions according to the invention may be used in two ways:

the first use consists in spreading the gel in the hands, applying it to the face or the body and then massaging it in the presence of water to develop the foam directly on the face or the body;

the other possible use of this type of product consists in developing the foam in the palm of the hands before applying it to the face or the body.

If the composition is sufficiently fluid, it may be packaged in a self-foaming airspray or aerosol can. The product is then delivered in the form of a foam which is applied directly to the skin or the hair.

In all cases, the foam is then rinsed off.

Another subject of the invention consists of a cosmetic process for cleansing the skin, the scalp and/or the hair, characterized in that the composition of the invention is applied to the skin, to the scalp and/or to the hair, in the presence of water, and in that the foam formed and the soiling residues are removed by rinsing with water.

The compositions according to the invention may also constitute a composition for treating greasy (or seborrhoeic) skin, especially when they contain a specific active agent for treating greasy skin, such as, for example, salicylic acid, azelaic acid, triclosan, piroctone olamine (octopirox), niacinamide (vitamin B3) or panthenol (vitamin B5).

Another subject of the invention is the use of the composition as defined above for the preparation of a composition for treating greasy skin.

PREPARATION EXAMPLES

Preparation of Ethoxylated (Meth)Acrylic Esters

These may especially be obtained by the action of glycidyl (meth)acrylate or (meth)acrylic acid or an alkyl (meth)acrylate or a (meth)acryloyl chloride on an ethoxylated fatty alcohol. Non-limiting examples which may be mentioned include the following preparations:

a) starting with glycidyl methacrylate and Genapol T-250;
b) starting with (meth)acrylic acid and Genapol UD-070;
c) starting with methyl (meth)acrylate and Genapol LA-090;

d) starting with (meth)acryloyl chloride and Genapol UC-070.

a) 500 g of Genapol T-250 and 75 g of glycidyl methacrylate are placed in a one-liter three-necked reactor equipped with a stirrer, a thermometer and a reflux condenser. The reaction mixture is heated at a temperature of 100° C. for 2 hours and the excess glycidyl methacrylate is removed by distillation under reduced pressure. The monomer obtained may be used for the polymerization without further purification.

b) 500 g of Genapol UD-070, 100 g of (meth)acrylic acid and p-toluenesulphonic acid as catalyst are placed in a one-liter three-necked reactor equipped with a stirrer, a thermometer and a reflux condenser. The reaction mixture is refluxed for 2 hours and the excess acid and the water formed during the reaction are separated out by distillation under reduced pressure. The monomer obtained may be used for the polymerization without further purification.

c) 500 g of Genapol LA-090, 100 g of methyl (meth)acrylate and 20 g of titanium tetraisopropoxide are placed in a one-liter three-necked reactor equipped with a stirrer, a thermometer and a reflux condenser. The reaction mixture is refluxed for 2 hours and, after separation by distilling off the alcohol formed, the remaining ester is distilled under reduced pressure. The monomer obtained may be used for the polymerization without further purification.

d) 500 g of Genapol UD-070, 110 g of (meth)acryloyl chloride and 50 g of sodium carbonate are placed in a one-liter three-necked reactor equipped with a stirrer, a thermometer and a reflux condenser. The reaction mixture is refluxed for 2 hours and the excess acid chloride is separated out by distillation under reduced pressure. The monomer obtained may be used for the polymerization without further purification.

Polymerization According to the Precipitation Method in Tert-Butanol 500 ml of tert-butanol and the calculated amount of AMPS are introduced into a 2-liter reactor equipped with a reflux condenser, a gas inlet, a thermometer and a stirrer. The mixture is neutralized by introducing $NH_3$, and the monomer prepared above is added to the reaction mixture. The reaction mixture is made inert by passing nitrogen or argon through, and, when the internal temperature has reached 60° C., the initiator (AIBN) is added to initiate the polymerization. After a few minutes, the polymer thus prepared precipitates. The mixture is maintained at reflux for 2 hours, and the polymer is separated from the solvent by vacuum filtration and then dried under reduced pressure.

The following polymers were prepared in the manner described above:

(starting with the following reagents in amounts expressed in grams)

| | | | | |
|---|---|---|---|---|
| Genapol T-250 methacrylate | 10 | 20 | 30 | 97 |
| AMPS neutralized with $NH_3$ | 90 | 80 | 90 | 3 |
| Methylenebisacrylamide (crosslinking agent) | | | 1.5 | |
| Allyl methacrylate (crosslinking agent) | | 1.7 | | |
| TMPTA (crosslinking agent) | 1.8 | | | 1.8 |
| Azobisisobutyronitrile (initiator) | | | 1 | |
| Dilauryl peroxide (initiator) | 1 | 1 | | |
| tert-Butanol | 300 | 300 | 300 | 300 |

Examples of the Cleansing Compositions

The examples which follow serve to illustrate the invention without, however, being limiting in nature. The amounts indicated are percentages by weight, except where otherwise mentioned. (A.M. means active material)

Example 1

Cleansing Gel

| | |
|---|---|
| Decyl glucoside (1) | 3% A.M. |
| Crosslinked copolymer of AMPS and of hexadecyl methacrylate 25 EO (2) | 1% A.M. |
| Water | qs 100% |

(1) APG: Alkyl (C9/11) polyglucoside (1.4) as a 40% solution, sold under the name Mydol 10 by the company Kao Chemicals;
(2) Copolymer crosslinked with allyl methacrylate and consisting of 80% by weight of AMPS units neutralized with $NH_3$ and 20% by weight of Genapol T-250 methacrylate units [units of formula (III) in which $R_1=CH_3$, $R_4=C_{16}-C_{18}$ and x=25].

The sensory qualities of the gel obtained were studied relative to comparative examples in which the copolymer according to the invention was replaced with polymers of the prior art.

Sensory performance: The volume of foam developed with the amphiphilic polymer used according to the invention is evaluated according to the protocol described below, compared (1) with a composition without polymer, (2) with a composition with an AMPS polymer not comprising a hydrophobic chain, and (3) with a composition with a carboxylic polymer comprising a hydrophobic chain.

The protocol is as follows: Before any use of the product, the hands are washed with household soap and then suitably rinsed and dried. Next, the protocol followed is as follows:

1—wet the hands by passing them under running water, and shake them three times to drain them,
2—place 1 g of product in the palm of one of the hands,
3—work the product between the two palms for 10 seconds,
4—add 2 ml of water and work the product again for 10 seconds,
5—rinse the hands under water,
6—wipe them.

The volume of foam developed in the hand is graded on a scale from 0 to 10 before rinsing, and the grade attributed is proportionately higher the greater the volume of foam.

In the table below, all the percentages are expressed by weight of active material (A.M.).

| Composition | Example 1 according to the invention | Comparative Example 1 | Comparative Example 2 | Comparative Example 3 |
|---|---|---|---|---|
| Decyl glucoside (1) | 3% A.M. | 3% A.M. | 3% A.M. | 3% A.M. |
| Crosslinked copolymer of AMPS and of hexadecyl methacrylate 25 EO | 1% A.M. | — | — | — |

-continued

| Composition | Example 1 according to the invention | Comparative Example 1 | Comparative Example 2 | Comparative Example 3 |
|---|---|---|---|---|
| (2) | | | | |
| Hostacerin AMPS (3) | — | — | 1% A.M. | — |
| Pemulen TR2 (4) | — | — | — | 0.5% A.M. |
| Water | qs 100% | qs 100% | qs 100% | qs 100% |
| Viscosity (Rheomat RM180, No. 3 spindle, at t 10 minutes) | 24.1 UD (= 0.8 Pa.s) | 0.0001 Pa.s | 11.3 UD (= 0.3 Pa.s) | 25.5 UD (= 0.9 Pa.s) |
| Volume of foam | 7/10 | 5.9/10 | 4.6/10 | 5.6/10 |

(1) APG: Alkyl (C9/11) polyglucoside (1.4) as a 40% solution, sold under the name Mydol 10 by the company Kao Chemicals;
(2) Copolymer crosslinked with allyl methacrylate and consisting of 80% by weight of AMPS units neutralized with $NH_3$ and 20% by weight of Genapol T-250 methacrylate units [units of formula (III) in which $R_1 = CH_3$, $R_4 = C_{16}$–$C_{18}$ and x = 25];
(3) Homopolymer of 2-acrylamido-2-methylpropane-sulphonic acid (CTFA name: Hostacerin AMPS) sold by the company Clariant;
(4) Hydrophobic-chain acrylic copolymer (CTFA name: Acrylates/C10–30 alkyl Acrylate Crosspolymer), sold by the company Goodrich.

It emerges from the above table that the compositions of the comparative examples give a much lower volume of foam than the example according to the invention. Furthermore, the polymer according to the invention makes it possible to obtain a viscous gel, more viscous than with the AMPS homopolymer in the same amount. The amphiphilic polymer used in the composition of the invention thus gives both an improvement in the volume of foam and good viscosity, which is particularly surprising when it is known that increasing the viscosity by adding a polymer generally has the consequence of reducing the volume of foam.

Example 2

Cleansing Composition

| Decyl glucoside (1) | 3% A.M. |
|---|---|
| Non-crosslinked copolymer of AMPS (2) | 1% A.M. |
| Water | qs 100% |

(1) APG: Alkyl (C9/11) polyglucoside (1.4) as a 40% solution, sold under the name Mydol 10 by the company Kao Chemicals;
(2) Non-crosslinked copolymer, consisting of 40% by weight of AMPS units neutralized with NH3 and of 60% by weight of Genapol® LA-030 methacrylate units [of formula (III) in which $R_1$=$CH_3$, $R_4$=$C_{12}$-$C_{14}$ and x=3].

The volume of foam obtained with this composition is 7.4/10; it is thus satisfactory. However, the composition is liquid like water (viscosity of 0.0001 Pa.s). This example thus shows that the amphiphilic polymers according to the invention, even when non-crosslinked, make it possible to improve the volume of foam, but that only the crosslinked polymers make it possible both to increase the volume of foam and to give a thickened composition.

Example 3

Cleansing Composition

| Cocobetaine (1) | 5% |
|---|---|
| Decyl glucoside (2) | 5% |
| Crosslinked copolymer of AMPS (3) | 1% |
| Glycerol | 5% |
| Preserving agent | qs |
| Water | qs 100% |

(1) Product sold under the name Empigen BB/FL by the company Albright & Wilson;
(2) APG: Alkyl (C9/11) polyglucoside (1.4) as a 40% solution, sold under the name Mydol 10 by the company Kao Chemicals;
(3) Allyl methacrylate-crosslinked copolymer, consisting of 80% by weight of AMPS units neutralized with $NH_3$ and of 20% by weight of Genapol T-250 methacrylate units [units of formula (III) in which $R_1$=$CH_3$, $R_4$=$C_{16}$-$C_{18}$ and x=25].

A creamy cleansing gel that gives a good quality of foam and that is pleasant to use is obtained.

The invention claimed is:

1. A composition comprising a (1) physiologically acceptable aqueous medium, (2) at least one surfactant chosen from the group consisting of alkylpolyglycosides, maltose esters, glycerolated fatty alcohols, N-alkylglucamine derivatives, amido ether carboxylates, acetates, alaninates, aspartates, glycinates, citrates, galacturonates, and fatty acid salts constituting soaps, and (3) at least one crosslinked amphiphilic polymer present in an amount sufficient to increase a volume of foam of the composition, said amphiphilic polymer is copolymer of AMPS and at least one ethylenically unsaturated hydrophobic monomer wherein said copolymer comprises at least one hydrophobic portion comprising from 6 to 50 carbon atoms.

2. The composition according to claim 1, wherein the hydrophobic part comprises from 6 to 22 carbon atoms.

3. The composition according to claim 2, wherein the hydrophobic part comprises from 6 to 18 carbon atoms.

4. The composition according to claim 3, wherein the hydrophobic part comprises from 12 to 18 carbon atoms.

5. The composition according to claim 1, wherein the ethylenically unsaturated hydrophobic monomer is an acrylate or an acrylamide of formula (I):

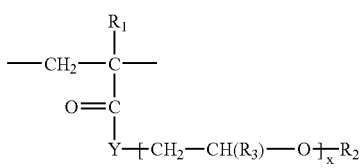

in which $R_1$ and $R_3$, may be identical or different, are a hydrogen atom or a linear or branched $C_1$-$C_6$ alkyl radical; Y is O or $NR_1$, $R_1$ having the meaning given above; $R_2$ is a hydrophobic hydrocarbon-based radical comprising at least from 6 to 50 carbon atoms; and x is from 0 to 100.

6. The composition according to claim 5, wherein the hydrophobic radical $R_2$ is chosen from the group consisting of linear $C_6$-$C_{18}$ alkyl radicals, branched $C_6$-$C_{18}$ alkyl radicals, cyclic $C_6$-$C_{18}$ alkyl radicals, $C_6$-$C_{18}$ alkylperfluoro radicals, cholesteryl radical, a cholesterol ester, and aromatic polycyclic groups.

7. The composition according to claim 5, wherein the monomer of formula (I) comprises at least one alkylene oxide unit and x is from 1 to 100.

8. The composition according to claim 5, wherein the monomer of formula (I) comprises at least one polyoxyalkylenated chain.

9. The composition according to claim 8, wherein the polyoxyalkylenated chain comprises ethylene oxide units and/or propylene oxide units.

10. The composition according to claim 9, wherein the polyoxyalkylenated chain consists of ethylene oxide units.

11. The composition according to claim 5, wherein the number of moles of alkylene oxide is from 3 to 100.

12. The composition according to claim 11, wherein the number of moles of alkylene oxide is from 3 to 50.

13. The composition according to claim 12, wherein the number of moles of alkylene oxide is from 7 to 25.

14. The composition according to claim 1, wherein the amphiphilic polymer of AMPS is selected from the group consisting of crosslinked copolymers comprising from 15% to 60% by weight of AMPS units and from 40% to 85% by weight of ($C_8$-$C_{16}$)alkyl(meth)acrylamide units, neutralized copolymers comprising from 15% to 60% by weight of AMPS units and from 40% to 85% by weight of ($C_8$-$C_{16}$) alkyl(meth)acrylamide units, non-neutralized copolymers comprising from 15% to 60% by weight of AMPS units and from 40% to 85% by weight of ($C_8$-$C_{16}$)alkyl(meth)acrylamide units, crosslinked copolymers comprising from 15% to 60% by weight of AMPS units and from 40% to 85% by weight of($C_{8\text{-}C16}$)alkyl (meth)acrylate units, neutralized copolymers comprising from 15% to 60% by weight of AMPS units and from 40% to 85% by weight of ($C_8$-$C_{16}$) alkyl (meth)acrylate units, non-neutralized copolymers comprising from 15% to 60% by weight of AMPS units and from 40% to 85% by weight of ($C_8$-$C_{16}$)alkyl (meth)acrylate units and terpolymers comprising from 10 mol % to 90 mol % of acrylamide units, from 0.1 mol % to 10 mol % of AMPS units and from 5 mol % to 80 mol % of n-($C_6$-$C_{18}$)alkylacrylamide units relative to the polymer.

15. The composition according to claim 1, wherein the amphiphilic polymer of AMPS is selected from the group consisting of crosslinked copolymers of partially neutralized AMPS, crosslinked totally neutralized AMPS, and crosslinked copolymers of n-dodecylmethacrylamide.

16. The composition according to claim 1, wherein the amphiphilic polymer of AMPS is a copolymer comprising 2-acrylamido-2-methylpropanesulphonic acid (AMPS) units of formula (II):

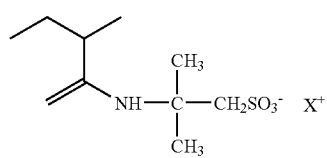

in which $X^+$ is a proton, an alkali metal cation, an alkaline-earth metal cation or an ammonium ion, and units of formula (III):

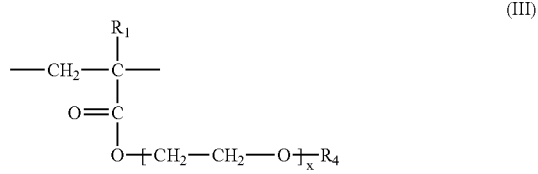

in which x is an integer of from 3 to 100; $R_1$ is a hydrogen atom or a linear or branched $C_1$-$C_6$ alkyl radical; and $R_4$ is a linear or branched $C_6$-$C_{22}$ alkyl.

17. The composition according to claim 16, wherein x=25, $R_1$ is methyl and $R_4$ is n-dodecyl, n-hexadecyl or n-octadecyl.

18. The composition according to claim 5, wherein the % molar proportion of units of formula (I) or of units of formula (III) in the polymer is from 50.1% to 99.9%.

19. The composition according to claim 5, wherein the % molar proportion of units of formula (I) or of units of formula (III) in the polymer is from 0.1% to 50%.

20. The composition according to claim 1, wherein the amount of amphiphilic polymer is from 0.01% to 50% by weight relative to the total weight of the composition.

21. The composition according to claim 1, wherein the surfactant is an alkylpolyglycoside represented by formula (IV):

$$R-O-(G)_x \qquad (IV)$$

in which R represents a linear or branched, saturated or unsaturated alkyl radical comprising from 6 to 30 carbon atoms, G represents a reduced sugar comprising from 5 to 6 carbon atoms, and x is a value ranging from 1 to 15.

22. The composition according to claim 21, wherein the alkylpolyglycoside is a compound of formula (IV) in which R is an alkyl radical comprising from 8 to 16 carbon atoms, G is glucose, fructose or galactose, and x is from 1 to 4.

23. The composition according to claim 1, wherein the surfactant is an alkylpolyglucoside.

24. The composition according to claim 1, further comprising one or more additional surfactants chosen from the group consisting of polycondensates of ethylene oxide on an alkyl chain, polycondensates of propylene oxide on an alkyl chain, fatty acid esters of polyols, alkoxylated alkamides, polyoxyethylenated carboxylic acid salts, sarcosinates, glutamates, alkyl sulphates, alkyl ether sulphates, sulphonates, isethionates, taurates, sulphosuccinates, alkyl sulphoacetates, polypeptides, anionic alkyl polyglucoside derivatives, and mixtures thereof.

25. The composition according to claim 1, wherein the total amount of surfactant is from 0.1% to 50% by weight relative to the total weight of the composition.

26. The composition according to claim 23, wherein the amount of alkylpolyglycoside is from 0.1% to 100% by weight relative to the total weight of surfactants.

27. The composition according to claim 1, wherein the physiologically acceptable medium comprises water or water and at least one organic solvent chosen from the group consisting of hydrophilic organic solvents, lipophilic organic solvents, amphiphilic solvents, and mixtures thereof.

28. The composition according to claim 1, further comprising at least one oily phase.

29. A cosmetic process for cleansing the skin, the scalp and/or the hair, comprising applying the composition according to claim 1 to the skin, to the scalp and/or to the hair, in the presence of water, and removing a foam formed and a soiling residue by rinsing with water.

30. The composition according to claim 5, wherein $R_1$ and $R_3$ are methyl.

31. The composition according to claim 5, wherein $R_2$ is a hydrophobic hydrocarbon-based radical comprising at least from 6 to 22 carbon atoms.

32. The composition according to claim 5, wherein $R_2$ is a hydrophobic hydrocarbon-based radical comprising at least from 6 to 18 carbon atoms.

33. The composition according to claim 5, wherein $R_2$ is a hydrophobic, hydrocarbon-based radical comprising at least from 12 to 18 carbon atoms.

34. The composition according to claim 16, wherein x is an integer of from 5 to 80.

35. The composition according to claim 16, wherein x is an integer of from 7 to 25.

36. The composition of claim 16, wherein $R_4$ is a linear or branched $C_{10}$-$C_{22}$ alkyl.

37. The composition according to claim 20, wherein the amount of amphiphilic polymer is from 0.1% to 20% by weight relative to the total weight of the composition.

38. The composition according to claim 20, wherein the amount of amphiphilic polymer is from 0.2% to 10% by weight relative to the total weight of the composition.

39. The composition according to claim 20, wherein the amount of amphiphilic polymer is from 0.25% to 5% by weight relative to the total weight of the composition.

40. The composition according to claim 22, wherein x is from 1 to 3.

41. The composition according to claim 25, wherein the total amount of surfactant is from 0.2% to 40% by weight relative to the total weight of the composition.

42. The composition according to claim 26, wherein the amount of alkylpolyglycoside is from 10% to 100% by weight relative to the total weight of surfactants.

43. A cosmetic process comprising cleansing the skin, the scalp and/or the hair with a shampoo, scrubbing product and/or exfoliant product comprising the composition according to claim 19.

44. A method of preparing a composition for treating greasy skin, said method comprising mixing the composition according to claim 1 with a preparation for treating skin.

45. A method for increasing the volume of foam in a composition comprising a surfactant, said method comprising mixing a crosslinked amphiphilic polymer comprising at least one ethylenically unsaturated monomer comprising a sulfonic group in a free form, a partially neutralized form or a totally neutralized form, with a composition comprising at least one surfactant chosen from the group consisting of alkylpolyglycosides, maltose esters, glycerolated fatty alcohols, N-alkylglucamine derivatives, amido ether carboxylates, acetates, alaninates, aspartates, glycinates, citrates, galacturonates, and fatty acid salts constituting soaps.

* * * * *

UNITED STATES PATENT AND TRADEMARK OFFICE
CERTIFICATE OF CORRECTION

PATENT NO. : 7,470,657 B2  Page 1 of 1
APPLICATION NO. : 10/181981
DATED : December 30, 2008
INVENTOR(S) : Veronique Guillou et al.

It is certified that error appears in the above-identified patent and that said Letters Patent is hereby corrected as shown below:

Column 19, line 39, "weight of($C_8$-$C_{16}$)alkyl (meth)acrylate units,"
should read -- weight of ($C_8$-$C_{16}$)alkyl (meth)acrylate units, --.

Signed and Sealed this

Twenty-fourth Day of March, 2009

JOHN DOLL
*Acting Director of the United States Patent and Trademark Office*